United States Patent [19]

Webb et al.

[11] Patent Number: 5,028,802
[45] Date of Patent: Jul. 2, 1991

[54] IMAGING APPARATUS AND METHODS UTILIZING SCANNABLE MICROLASER SOURCE

[75] Inventors: Robert H. Webb; Francois C. Delori, both of Lincoln; George T. Timberlake, Natick, all of Mass.

[73] Assignee: Eye Research Institute of Retina Foundation, Boston, Mass.

[21] Appl. No.: 464,352

[22] Filed: Jan. 11, 1990

[51] Int. Cl.$^5$ .............................................. G01N 21/86
[52] U.S. Cl. ..................................... 250/571; 362/227
[58] Field of Search ...................... 250/571, 578.1, 561; 362/227, 230, 236, 238; 358/475, 480; 350/96.11

[56] References Cited

U.S. PATENT DOCUMENTS

| | | | |
|---|---|---|---|
| 4,213,678 | 7/1980 | Pomerantzeff et al. | 351/7 |
| 4,360,921 | 11/1982 | Scifres et al. | 350/96.11 |
| 4,639,608 | 1/1987 | Kuroda | 358/475 |
| 4,764,005 | 8/1988 | Webb et al. | 351/205 |
| 4,882,498 | 11/1989 | Cochran | 250/571 |

OTHER PUBLICATIONS

"Tandem-Scanning Reflective-Light Microscope", Petran et al., *Journal of the Optical Society of America*, vol. 58, May, 1968, pp. 661–664.
Webb et al., "Confocal Scanning Laser Ophthalmoscope", *Applied Optics*, vol. 26, Apr. 15, 1987, pp. 1492–1499.
*The Handbook of Biological Confocal Microscopy*, Pawley, ed., IMR Press, 1989.
Ozberkman, "New-Micro-Lasers Debut", *Optical News*, Oct. 1989, p. 30.

*Primary Examiner*—David C. Nelms
*Assistant Examiner*—Khaled Shami
*Attorney, Agent, or Firm*—Lahive & Cockfield

[57] ABSTRACT

Apparatus and methods for generating an image of an object utilize a scannable microlaser array to provide a flying spot light source. The microlaser array is scan-energized and imaged onto the object to illuminate the object. Light scattered, reflected, or transmitted from the object is collected and detected, and can be converted to a video-level signal for display on a monitor. The microlaser array can be raster-scanned, scanned in a random access mode, or have at least two laser elements energized simultaneously, to enhance contrast, provide multiplexing, and increase dynamic range. A confocal configuration utilizes a detector array that is scan-read synchronously with the laser excitation pattern.

30 Claims, 3 Drawing Sheets

IMAGING APPARATUS AND METHODS UTILIZING SCANNABLE MICROLASER SOURCE

BACKGROUND OF THE INVENTION

This invention relates generally to optical instruments and methods, and, more particularly, relates to apparatus and methods for scanning a surface or other object with an optical beam, detecting the light emitted from or transmitted by the object, and generating an image of the object.

Scanning imaging techniques are employed in scanning laser microscopes (SLM), confocal scanning laser microscopes (CSLM), tandem scanning confocal microscopes (TSM), scanning laser ophthalmoscopes (SLO), flying spot television (FSTV) devices, and other applications. Confocal imaging systems can provide enhancements in contrast and in dynamic range. Certain of these imaging systems include moving optical elements for deflecting a laser beam, so that an illumination spot is swept across the object to be scanned. Other such systems employ mechanical elements to rotate an illuminated pinhole for the same purpose. In the TSM, a plurality of illumination spots is moved simultaneously, to provide source multiplexing, necessary because the source does not have the higher radiance (brightness) of a laser.

A double scanning optical apparatus is disclosed in U.S. Pat. No. 4,764,005 of Webb et al. The apparatus utilizes multiple scanning elements, including a multi-faceted rotating polygonal reflector scanner, to provide scanning of both incident and reflected light at television-rate frequencies.

Additionally, certain flying spot imagers use a cathode ray tube (CRT) as a light source, with a single illuminated point scanned across the CRT face. The tube face is imaged onto the object to provide the illumination raster.

A TSM is discussed in Petran et al., "Tandem-Scanning Reflected-Light Microscope," *Journal of the Optical Society of America*, Vol. 58, No. 5, pp. 661–664, May 1968. Petran et al. acknowledge that reflected-light microscopy of semi-transparent material is usually unsatisfactory because of low contrast and light scattering, and describe the TSM, in which both the object plane and the image plane are scanned in tandem. As a result, only light reflected from the object plane is included in the image. In the Petran et al. system, the object is illuminated with light passing through holes in one sector or side of a rotating scanning disk, known as a Nipkow disc. The scanning disk is imaged by the objective at the object plane. Reflected-light images of these spots are directed to the diametrically opposite side of the same disk. Light can pass from the source to the object plane, and from the object plane to the image plane, only through optically congruent holes on diametrically opposite sides of the rotating disk. This configuration produces an image having enhanced contrast and sharpness relative to a conventional reflected-light microscope.

Tandem scanning confocal arrangements and flying spot CRT configurations, however, are "light-starved" by the limited brightness of the illumination spot. In TSM configurations, this brightness limitation is partially compensated by the multiplex operation. TSM systems, however, are hampered by stray light scattered from the moving pinhole array.

Current flying spot systems benefit from the advent of the laser. A number of scanning laser ophthalmoscopes (SLO), for example, employ a laser beam scanned by moving electromechanical elements. A scanning ophthalmoscope of this type is disclosed in U.S. Pat. No. 4,213,678 of Pomerantzeff et al. The ophthalmoscope discussed therein utilizes a laser source to produce a narrow output beam, and a mechanical device for scanning the beam across the fundus of an eye. A confocal scanning laser ophthalmoscope (CSLO) is disclosed in Webb et al., "Confocal Scanning Laser Ophthalmoscope," *Applied Optics*, Vol. 26, No. 8, Apr. 15, 1987, pp. 1492–1499. The CSLO scans an illumination spot over the object of interest, and synchronously scans a detector over the image. Other confocal devices, are discussed in *The Handbook of Biological Confocal Microscopy*, Pawley, ed., IMR Press, 1989.

Conventional scanning laser devices, however, necessitate a multiplicity of mechanical components moving at high speed. They are typically bulky, require significant power to drive the scanning mechanism, and generally provide only a predetermined scanning pattern.

It is accordingly an object of this invention to provide improved scanning-type imaging methods and apparatus.

A further object of the invention is to provide such methods and apparatus affording high spatial resolution, enhanced brightness, increased dynamic range, and a selectable, or random-access, scanning pattern.

It is another object of the invention to provide such imaging methods and apparatus capable of being implemented in a compact and reliable embodiment.

A further object of the invention is to provide display or illumination devices having high brightness.

Other general and specific objects of the invention will in part be obvious and will in part appear hereinafter.

SUMMARY OF THE INVENTION

The invention attains the foregoing objects with methods and apparatus for generating an image of an object with scanned illumination. One aspect of the invention includes an array of independently excitable light sources, optical elements for directing the light generated by the light source array onto the object, and a detecting module for detecting light that is transmitted, reflected, or scattered from the object when the object is illuminated by the illumination array and the optical elements. The source array, optical elements and detecting module can be, and preferably are, stationary relative to one another and relative to the object.

In one practice of the invention, the array element is an array of microlasers. The microlasers can be addressed in a raster pattern or, in another embodiment, in a random-access pattern. The invention can further include an excitation element, in electrical communication with the microlasers, for exciting the microlasers in a selected scanning pattern. The excitation element, moreover, can simultaneously excite more than one microlaser.

In a further aspect of the invention, the detecting module includes optical elements for collecting scattered, reflected, or transmitted light from the object, and for directing the collected light onto a photoelectric transducer or detector element that converts the light into an electrical signal. The transducer can, by way of example, be a photomultiplier tube (PMT) or avalanche photodiode (APD). The transducer can convert the collected light into video-level electrical signals, and the invention can further include a video monitor for displaying a video image representative of the collected light, in response to the video-level electrical signals. The invention can be practiced with other video output peripheral devices, including a computer frame grabber for digitizing the image information from the transducer and for storing it in computer memory.

A confocal scanning embodiment of the invention utilizes an image dissector tube as the detector module. This device has a plurality of independently selectable photosensitive regions. The regions are selected substantially synchronously with the excitation scanning pattern.

Another confocal scanning configuration in accordance with the invention utilizes a detector array having independently addressable photosensitive regions. These photosensitive regions are read individually, in a pattern that is synchronized with the scanning excitation pattern. Detectors of this type include photodiode arrays, MAMA arrays, and non-integrating CCD arrays modified to have independently addressable regions.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF ILLUSTRATED EMBODIMENTS

The invention provides scanning imaging methods and apparatus that employ microlasers in a scanning mode as the illumination source, advantageously exploiting the high brightness or radiance of the laser. The invention preferably includes an array of microlaser sources like that depicted in FIGS. 1A and 1B.

Figure 1A:
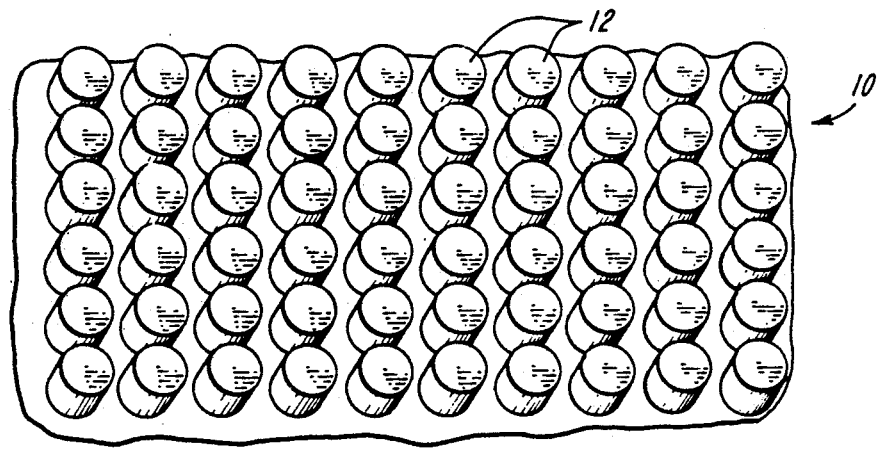
FIGS. 1A and 1B are schematic diagrams depicting a scannable microlaser source utilized in accordance with the invention.
Figure 1B:
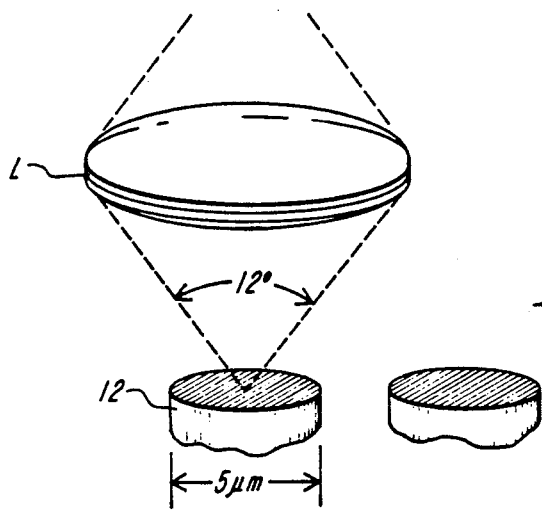
Figure 1C:
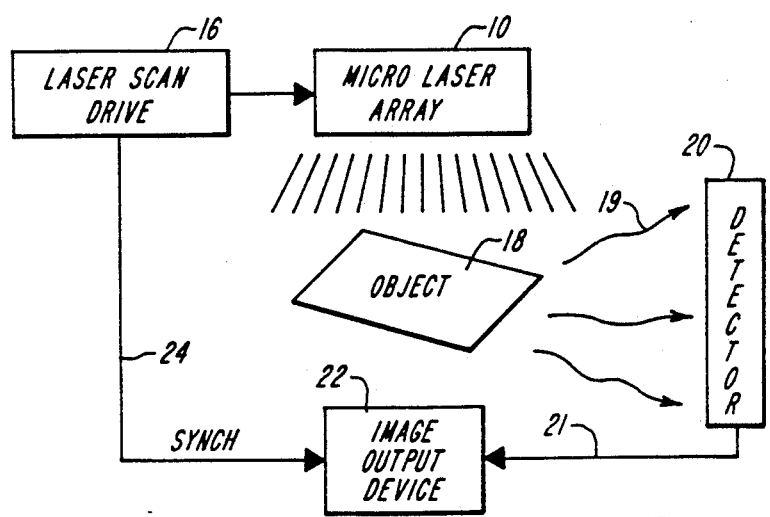
FIGS. 1C is a block diagram depicting scanning laser apparatus utilizing the microlaser source of FIG. 1.

Referring to FIGS. 1A and 1B, a preferred practice of the invention uses an $N \times M$ array 10 of microlasers 12, where N and M are typically in the range of 500 to 1,000, although other values can be used. Such microlasers can be, for example, low threshold electrically-pumped vertical-cavity surface-emitting diode lasers. A two-dimensional microlaser array of this embodiment is contained on an integrated circuit fabricated by AT&T Bell Laboratories, Murray Hill, N.J. The lasers emit light perpendicularly to the surface of the chip. Each square centimeter of the chip contains approximately two million individual lasers.

Current microlaser arrays consist of two interference mirrors formed by alternating layers of aluminum arsenide and gallium arsenide, around a 10-nanometer thick active region of indium gallium arsenide, all grown on a gallium arsenide substrate. This structure is covered with a gold electrical contact and etched by chemically-assisted ion beam lithography to form cylindrical lasers. The threshold current required to induce lasing is approximately three kiloamperes per square centimeter. See Ozberkmen, "New Micro-Lasers Make Debut," *Optics News*, October 1989, p. 30.

A preferred practice of the invention utilizes a microlaser source array 10 in which the individual lasers have diameters of between one to five micrometers, as indicated in FIG. 1B. A five micrometer diameter laser is well suited for an ophthalmoscopic application for illuminating the eye, while a one micrometer diameter provides enhanced throughput matching for the resolution of microscopy. In a typical embodiment, the microlasers are two micrometers in diameter on centers two micrometers apart, so that a 512 by 512 array, for example, is approximately one millimeter square. Those skilled in the art will appreciate that a $512 \times 512$ array can be imaged to provide a level of resolution compatible with current TV, and that proposed high-definition television (HDTV) standards will require a $1024 \times 1024$ array.

The microlaser array is preferably incorporated in conjunction with one or more lenses L, as shown in FIG. 1B, in scanning laser configurations as depicted in FIGS. 1C-4. The embodiment shown in FIG. 1C includes laser scan drive 16 for energizing the lasers of array 10. The microlasers can be energized sequentially, for instance, so that the array is scanned in a conventional TV raster fashion, at TV scan rates. The array is imaged on the object 18 to be illuminated, thereby providing raster illumination of the object. Light 19 emitted from the object, by reflection, scatter or transmission, is then detected by detector 20 and the detection signal, carried on line 21, is displayed synchronously with the array scan, to provide a video image on a monitor or other image output device 22 driven by SYNCH signals provided by drive 16 on line 24.

Illumination and imaging apparatus in accord with the invention can be configured in reflection or transmission modes. In particular, FIGS. 2 and 3 depict reflection embodiments, while FIG. 4 shows an implementation utilizing light transmission.

Figure 2:
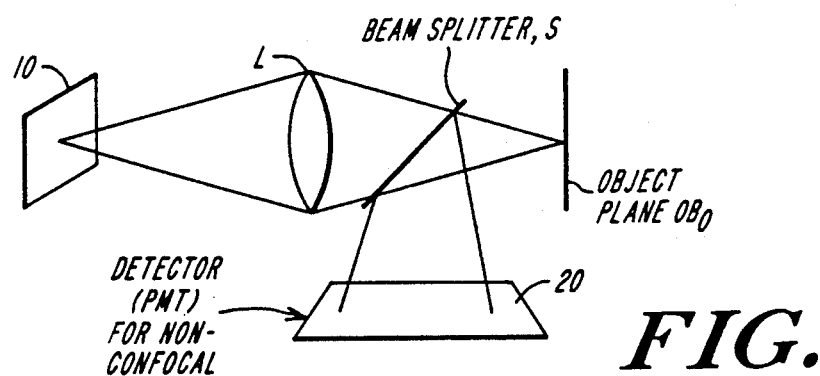
FIG. 2 shows scanning laser microscope (SLM) apparatus constructed in accordance with the invention, employing the microlaser source of FIG. 1.
Figure 3:
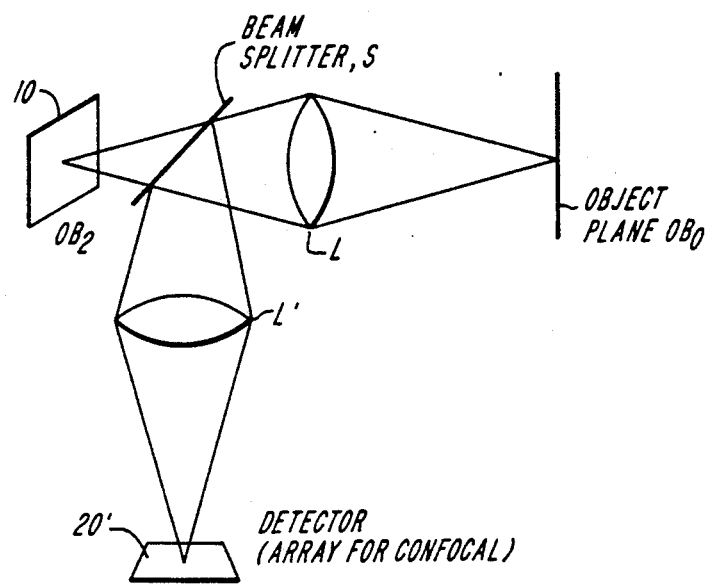
FIG. 3 depicts a confocal scanning microscope (CSM) embodiment of the invention.

In the embodiment shown in FIGS. 2 and 3, lens L directs light from scanned source array 10 onto the object plane $OB_o$, and light reflected from the object is directed to detector 20 by beam splitter S. The confocal configuration depicted in FIG. 3 employs a lens L' to direct light reflected from the object onto discrete regions of a detector array 20' configured in a manner discussed below.

Figure 4:
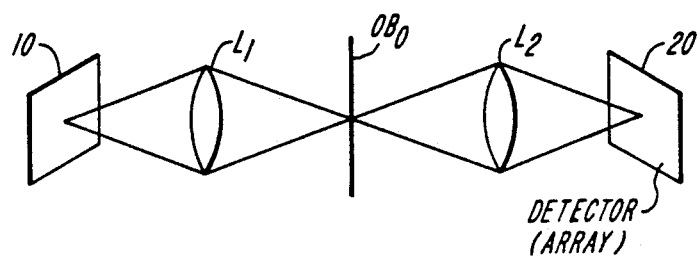
FIG. 4 depicts an implementation of the invention utilizing light transmission.

The transmission embodiment depicted in FIG. 4 employs lens L1 to direct light onto the object plane $OB_o$, and light transmitted through the object is collected and directed by lens L2 onto the detector array 20.

Referring again to FIG. 1C, the sequential raster scanning provided by scan drive 16 can be varied in accord with a preferred practice of the invention, to provide random access excitation of the microlasers, while maintaining the above-described optical characteristics of the system. A selected random access excitation permits selected object points to be illuminated more often than others, thus increasing dynamic range by avoiding brighter areas, and accommodating problems of light bleaching.

Various types and sizes of optical focusing elements can be utilized in accordance with the invention, depending upon the desired application of the imaging device. In an ophthalmic application, as depicted in FIG. 5, the microlaser array 10 can be imaged onto a patient's retina, and scanned to illuminate the retina, thereby providing a no-moving-parts laser scanner for a scanning laser ophthalmoscope (SLO) or scanning laser microscope (SLM).

Figure 5:
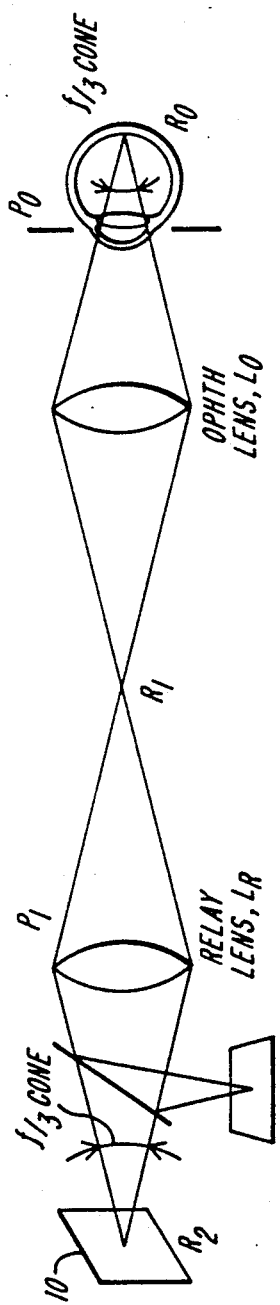
FIG. 5 shows a scanning laser ophthalmoscope (SLO) constructed in accordance with the invention.

In particular, to construct an SLO as illustrated in FIG. 5, optical components can be selected in accordance with conventional practice to provide an epitaxial f/3 optical system. The illuminating microlaser array 10 can be placed at a retinal conjugate plane, $R_2$, approximately thirty millimeters in front of the relay lens $L_R$ located at a pupilary conjugate $P_1$. The light collected by the relay lens $L_R$ passes through the pupil of the eye at $P_O$, where the ophthalmic lens $L_0$ images the relay lens. The eye itself re-images the retinal conjugates $R_2$ and $R_1$ on the retina $R_O$.

Alternatively, the source array can be placed at $R_1$ and the relay lens omitted. The relay lens is provided to accommodate the instrument to the inflexible throughput of the eye.

Currently available microlaser sources generate light having a wavelength of approximately 983 nanometers. At this wavelength, an f/2 optical system imaging the microlaser array 10 can have a lateral resolution of approximately 1.8 micrometers, and an axial resolution of approximately 23.5 micrometers. Higher resolution can be obtained by utilizing standard microscope optical elements, possibly at the cost of reduced light throughput. The extension of microlaser technology to shorter wavelengths will enable the microlaser-illuminated systems depicted in FIGS. 2-5 to attain higher spatial resolution with a given set of optical elements.

Apparatus constructed in accordance with the invention can be further enhanced by replacing the conventional detector element 20 with a scan-addressable detector 20', such as a detector array that can be read in the same sequence as the excitation of the illuminator array, thus producing a confocal configuration. A confocal embodiment of the invention is depicted in FIG. 3.

Various detectors can be utilized in accord with the invention. Detector selection is dependent upon whether the device is configured as a scanning microscope or a confocal scanning microscope. A scanning microscope can utilize a photomultiplier tube (PMT) or a single avalanche photodiode (APD) or other photoelectric detector. A confocal scanning microscope can employ an image dissector tube or one of its solid state analogs such as a scanned photodiode array, discussed below.

In particular, a detector for non-confocal apparatus can be a photomultiplier tube (PMT) such as an RCA Type 4526, a pin diode type photodetector such as a United Detector Technology Type PIN-020A, or an APD such as the RCA Type C30950. The photosensitive surface of the PMT is aligned with the scanning laser beam in accord with conventional photodetector practice. Techniques for implementing this type of detection system are known in the art.

A confocal embodiment of the invention, as depicted in FIG. 3, utilizes a confocal detector 20' consisting of an image dissector tube, or low spatial resolution energy detection device, such as Hammatsu Type R-571 manufactured in Japan. An image dissector tube is a (PMT) having a selectable sensitive spot. In a confocal embodiment of the invention, the photosensitive region is selected synchronously with the scanning illumination of the object by the scanning laser beam. Thus, light scattered from non-illuminated portions of the object does not contribute to the output of the detection device, unless it impinges upon the selected portion of the detector. As a result, noise due to unwanted scattered light is significantly reduced.

In a further preferred practice, the detector 20' is an array of solid-state photodiodes, such as avalanche photodiodes (APD). A 25 element APD array is currently in use in a confocal embodiment of the invention.

Alternatively, the confocal detector 20' can be a multi-node micro-channel array (MAMA) or can employ CCD or SID arrays modified to be non-integrating or randomly addressable. Those skilled in the art will appreciate that the randomly-addressable detector arrays of the invention can provide the advantages of confocal microscopy in a compact solid-state system.

Moreover, in a confocal embodiment having an addressable array detector according to FIG. 3, by exciting more than one microlaser simultaneously, the full multiplex advantage of the TSM can be realized. For example, by energizing one percent of the lasers in the array at any one point in the scan cycle—i.e., by energizing 2500 microlasers simultaneously in a 250,000 microlaser array (500×500)—much of the confocal contrast enhancement is available, and the actual scan can be made 100 times faster or 100 times brighter. Thus, while conventionally illuminated TSM systems suffer from light starvation, a multiplexed microlaser-illuminated system according to the invention eliminates this deficiency and other TSM problems, including stray light scattered from the moving pinhole array. It thus has all the advantages of an SLM and of a TSM.

As discussed above, a preferred embodiment of the invention utilizes microlasers of two micrometers in diameter, two micrometers apart, so that a 500 by 500 array is one millimeter square. Imaged at unity magnification, this provides a microscope having two micrometers resolution. This exemplifies the coherence of the non-overlapping light beams generated by the microlaser light source and the resulting zero degradation of the light energy. Minified ten times, the microscope will have a resolution equal to a currently available light microscope. Magnified ten times, the array provides an excellent biomicroscope, or a machinist's microscope. Magnified 100 times, the system can be a TV camera having a ten-centimeter field.

Figure 6:
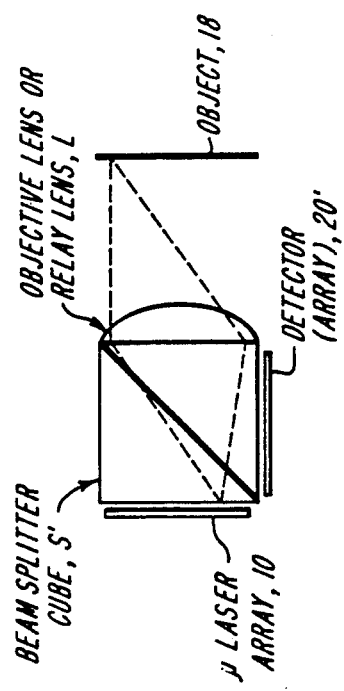
FIG. 6 depicts another embodiment of imaging apparatus in accordance with the invention.

Because the entire system can be implemented with one solid state device, a microscope constructed in accordance with the invention can be as small as a few millimeters in size. In particular, a confocal scanning laser microscope can be housed in a container approximately the size of a 35-millimeter film canister, or less. This compact size renders the invention especially useful for remote sensing applications, endoscopy, headmounted SLO applications, a hand-held inspection microscope, and many other applications requiring a small imaging apparatus. FIG. 6 depicts a compact embodiment of the invention, utilizing microlaser source array 10 and detector array 20' coupled to adjacent surfaces of a beam splitter cube S', and an objective lens or relay lens L coupled to the objective surface of the beam splitter cube. Lens L directs light from the source array 10 to the object 18, and, in conjunction with splitter S', directs light reflected by object 18 to detector array 20', scanned in synchrony with the scanning of microlaser array 10.

Figure 7:
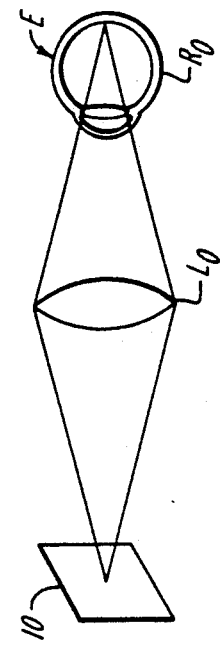
FIG. 7 shows a display device utilizing the scannable microlaser source of FIG. 1.

In another practice of the invention, shown in FIG. 7, microlaser source 10 can be utilized in "heads-up" display configuration, illuminating an object such as the eye E via opthalmic lens $L_o$.

Those skilled in the art will recognize that variants of the illustrated embodiments can be constructed using other scannable or randomly accessible illumination sources. One such variation uses an array of laser beams created by multiple reflection—generated, for example, by a source beam splitter—or by diffraction. The beam array can be scanned mechanically over a small scan angle. This configuration employs the brightness of laser sources and can provide the multiplex advantage, depending upon the detector selected.

It will thus be seen that the invention efficiently attains the objects set forth above, among those made apparent from the preceding description. It will be understood that changes may be made in the above construction and in the foregoing sequences of operation without departing from the scope of the invention. For example, while the invention has been described in connection with surface-emitting diode lasers, the invention can also be practiced with other scannable light source arrays. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of lanquage, might be said to fall therebetween.

Having described the invention, what is claimed as new and secured by letters patent is:

1. A thin film metal alloy rigid magnetic recording disk comprising:
   a substrate;
   a magnetic layer comprising a cobalt-based alloy formed over the substrate; and
   a protective overcoat formed over the magnetic layer, the ovrcoat being a film having a substantially planar surface and comprising primarily carbon in the essentially amorphous form and one or more of tungsten (W) or tungsten carbide (WC) distributed throughout and embedded within the carbon, the tungsten as temperature carbide being present in the carbon in the range of approximatley 4 to approximately 12 atomic percent and in the form of clusters which project above the substantially planar surface of the overcoat film.

2. In apparatus according to claim 1, the further improvement wherein
   ones of said microlasers are addressable by electrical excitations in an excitation scanning pattern, and
   further comprising excitation means, in electrical communication with said light source elements, for generating time-variant electrical excitations and addressing said electrical excitations to ones of the light source elements in a excitation scanning pattern.

3. In apparatus according to claim 2, the further improvement wherein said microlasers are addressable in a raster excitation pattern, and
   said excitation means addresses said electrical excitations to ones of the microlasers in a raster excitation pattern.

4. In apparatus according to claim 2, the further improvement wherein said microlasers are addressable in a random-access excitation pattern, and
   said excitation means addresses said electrical excitations to ones of the microlasers in a random-access excitation pattern.

5. In apparatus according to claim 2, the further improvement wherein said detecting means comprises
   light collector means for collecting said light resulting from any of light scattering, light reflection, or light transmission from the object, and for directing said collected light onto an image plane, and
   transducer means for converting said collected light into an electrical signal.

6. An improved contact start/stop (CSS) magnetic recording rigid disk file wherein the improvement comprises at least one thin film metal alloy magnetic recording disk having a protective overcoat with a substantially planar surface and comprising essentially amorphous carbon or essentially amorphous hydrogenated carbon, the overcoat containing approximately 4 to approximately 12 atomci percent tungsten or tungsten carbide present as clusters which project above the substantially planar surface of the overcoat.

7. In apparatus according to claim 5, the further improvement wherein said transducer means includes an avalanche photodiode.

8. In apparatus according to claim 5, the further improvement wherein said transducer means includes a plurality of independently selectable photosensitive regions, and means for selecting said independently selectable photosensitive regions substantially synchronously with the excitation scanning pattern.

9. In apparatus according to claim 8, the further improvement wherein said transducer means includes an image dissector.

10. In apparatus according to claim 8, the further improvement wherein said detector array includes an array of photodiodes.

11. In apparatus according to claim 8, the further improvement wherein said detector array includes a multi-anode micro-channel array.

12. In apparatus according to claim 8, the further improvement wherein said detector array includes a non-integrating charge-storing photoelectric semiconductor array having independently read-addressable regions.

13. In apparatus according to claim 5, the further improvement wherein said transducer means includes means for converting said collected light into video-level electrical signals, and
    further comprising video display electrical communication with said transducer means, for displaying a video image representative of said collected light, in response to said video-level electrical signals.

14. A method for generating an image of an object, the method comprising the steps of
    generating time-variant electrical excitations, addressing said electrical excitations to microlasers in an array of independently addressable microlasers to generate non-overlapping beams of coherent light, directing said light onto the object, and detecting light resulting from any of light scattering, light reflection, or light transmission from the object.

15. In apparatus for generating non-overlapping beams of coherent an image of an object, the improvement comprising illumination means for generating light, said illumination means including an array means, said array means including an array of independently addressable microlasers for generating light in response to electrical excitations addressed to any of the microlasers, said microlasers being addressable by electrical excitations in an excitation scanning pattern, excitation means, in electrical communication with said microlasers, for generating time-variant electrical excitations and addressing said electrical excitations to ones of the microlasers in an excitation scanning pattern, said excitation means addressing said electrical excitations simultaneously to more than one of said microlasers, focusing means for directing said light generated by the illumination means onto the object, and detecting means for detecting light resulting from any of light scattering, light reflection, or light transmission from the object when the object is illuminated by said light generated by said illumination means and directed by said focusing means onto the object.

16. In apparatus according to claim 15, the further improvement wherein said microlasers are addressable in a raster excitation pattern, and said excitation means addresses said electrical excitations to the microlasers in a raster excitation pattern.

17. In apparatus according to claim 15, the further improvement wherein said microlasers are addressable in a random-access excitation pattern, and said excitation means addresses said electrical excitations to the microlasers in a random-access excitation pattern.

18. In apparatus according to claim 15, the further improvement wherein said detecting means comprises light collector means for collecting said light resulting from any of light scattering, light reflection, or light transmission from the object, and for directing said collected light onto an image plane, and transducer means, located substantially in said image plane, for converting said collected light into an electrical signal.

19. In apparatus according to claim 18, the further improvement wherein said transducer means includes a plurality of independently selectable photosensitive regions, and means for selecting said independently selectable photosensitive regions substantially synchronously with the excitation scanning pattern.

20. In apparatus according to claim 19, the further improvement wherein said transducer means includes an image dissector.

21. In apparatus according to claim 19, the further improvement wherein said detector array includes an array of photodiodes.

22. In apparatus according to claim 19, the further improvement wherein said detector array includes a multi-anode micro-channel array.

23. In apparatus according to claim 19, the further improvement wherein said detector array includes a non-integrating charge-storing photoelectric semiconductor array having independently read-addressable regions.

24. In apparatus according to claim 19, the further improvement wherein said transducer means includes means for converting said collected light into video-level electrical signals, and further comprising video display means, in electrical communication with said transducer means, for displaying a video image representative of said collected light, in response to said video-level electrical signals.

25. A method of generating an image of an object, the excitations, addressing said electrical excitations simultaneously to at least two microlasers in an array of independently addressable microlasers in an excitation scanning pattern to generate non-overlapping beams of coherent light, directing said light onto the object, and detecting light resulting from any of light scattering, light reflection, or light transmission from the object.

26. In apparatus according to claim 4, the further improvement wherein said excitation means includes means for controlling said excitation pattern to reduce the brightness of brighter areas of the image, so that light bleaching is reduced.

27. In apparatus for generating an image of an object, the improvement comprising scannable illumination means for generating light, said scannable illumination means including a laser for generating non-overlapping beams of coherent light in response to electrical excitations addressed to said laser, excitation means, in electrical communication with said laser, for generating time-variant electrical excitations and addressing said electrical excitations to said laser in an excitation scanning pattern, and multiplexing means, coupled to said excitation means and said scannable illumination means, for multiplexing said light generated by said laser to generate a time-variant array of laser beams, focusing means for directing said light generated by said illumination means onto the object, and detecting means for detecting light resulting from any of light scattering, light reflection, or light transmission from the object when the object is illuminated by said light generated by said scannable illumination means and directed by said focusing means onto the object.

28. In apparatus according to claim 27, the further improvement wherein said multiplexing means includes beam splitter means, optically coupled to said laser, for generating a plurality of laser beams from said light generated by said laser.

29. In apparatus according to claim 27, the further improvement wherein said multiplexing means includes diffraction means, optically coupled to said laser, for diffracting said light generated by said laser through a selected angle of diffraction.

30. In apparatus according to claim 27, the further improvement comprising array scanning means, coupled to said multiplexing means, for scanning said array of laser beams over a selected scan angle.

* * * * *

UNITED STATES PATENT AND TRADEMARK OFFICE
CERTIFICATE OF CORRECTION

PATENT NO. : 5,028,802
DATED : July 2, 1991
INVENTOR(S) : Robert H. Webb, Francois C. Delori and George T. Timberlake It is certified that error appears in the above-identified patent and that said Letters Patent is hereby corrected as shown below:

Column 7, lines 47-62, replace claim 1 with the following:

1. In apparatus for generating an image of an object, the improvement comprising
illumination means for generating light, said illumination means including an array means, said array means including an array of independently addressable microlasers, for generating non-overlapping beams of coherent light in response to electrical excitations addressed to any of the microlasers,
focusing means for directing said light generated by the illumination means onto the object, and
detecting means for detecting light resulting from any of light scattering, light reflection, or light transmission from the object when the object is illuminated by said light generated by said illumination means and directed by said focusing means onto the object.

Column 8, lines 25-34, replace claim 6 with the following

6. In apparatus according to claim 5, the further improvement wherein said transducer means includes a photomultiplier tube.

UNITED STATES PATENT AND TRADEMARK OFFICE
CERTIFICATE OF CORRECTION

PATENT NO. : 5,028,802
DATED : July 2, 1991
INVENTOR(S) : Robert H. Webb, Francois C. Delori and George T. Timberlake It is certified that error appears in the above-identified patent and that said Letters Patent is hereby corrected as shown below:

Column 8, line 62 (claim 13), after "display" insert --means, in---.

Column 9, lines 9-10 (claim 15), delete "non-overlapping beams of coherent"; and line 15, after "generating", insert --non-overlapping beams of coherent--.

Column 10, line 18 (claim 25), delete "excitations," and insert --method comprising the steps of
      generating time-variant electrical excitations---.

Column 8, claim 12, line 55, between "non-integrating" and "charge-storing", insert --or--.

Signed and Sealed this

Twenty-ninth Day of June, 1993

Attest:

MICHAEL K. KIRK

*Attesting Officer*     *Acting Commissioner of Patents and Trademarks*